United States Patent
Erdman

(10) Patent No.: US 7,727,207 B2
(45) Date of Patent: Jun. 1, 2010

(54) DISPOSABLE ARTICLE WITH CENTRALLY LOCATED ZONES OF ELASTICITY

(75) Inventor: Carol L Erdman, West Chester, PA (US)

(73) Assignee: Paragon Trade Brands, LLC, Great Neck, NY (US)

( * ) Notice: Subject to any disclaimer, the term of this patent is extended or adjusted under 35 U.S.C. 154(b) by 474 days.

(21) Appl. No.: 10/607,975

(22) Filed: Jun. 30, 2003

(65) Prior Publication Data

US 2004/0267222 A1 Dec. 30, 2004

Related U.S. Application Data

(62) Division of application No. 09/989,447, filed on Nov. 21, 2001, now abandoned.

(51) Int. Cl.
*A61F 13/15* (2006.01)
*A61F 13/20* (2006.01)

(52) U.S. Cl. ............. 604/385.01; 604/358; 604/385.29; 604/385.3; 604/385.31

(58) Field of Classification Search ............ 604/385.01, 604/385.16, 385.21–385.31
See application file for complete search history.

(56) References Cited

U.S. PATENT DOCUMENTS

| | | | | |
|---|---|---|---|---|
| 3,098,484 A | * | 7/1963 | Younger | 604/396 |
| 4,205,679 A | * | 6/1980 | Repke et al. | 604/366 |
| 4,655,760 A | * | 4/1987 | Morman et al. | 604/385.26 |
| 4,861,652 A | * | 8/1989 | Lippert et al. | 428/152 |
| 4,938,753 A | * | 7/1990 | Van Gompel et al. | 604/385.29 |
| 5,221,277 A | * | 6/1993 | Beplate | 604/394 |
| 5,451,219 A | * | 9/1995 | Suzuki et al. | 604/385.22 |
| 5,500,063 A | * | 3/1996 | Jessup | 156/85 |
| 5,554,143 A | | 9/1996 | Roe et al. | |
| 5,669,996 A | * | 9/1997 | Jessup | 156/85 |
| 5,746,731 A | | 5/1998 | Hisada | |
| 5,766,411 A | | 6/1998 | Wilson | |
| 5,985,070 A | | 11/1999 | Boberg | |
| 6,168,585 B1 | * | 1/2001 | Cesco-Cancian | 604/385.26 |
| 6,210,387 B1 | | 4/2001 | Rudberg et al. | |
| 6,231,557 B1 | * | 5/2001 | Krautkramer et al. | 604/385.16 |
| 6,245,401 B1 | * | 6/2001 | Ying et al. | 428/58 |
| 6,316,687 B1 | * | 11/2001 | Davis et al. | 604/372 |
| 6,413,249 B1 | * | 7/2002 | Turi et al. | 604/387 |
| 6,676,957 B1 | * | 1/2004 | Resheski-Wedepohl et al. | 424/430 |
| 2001/0021836 A1 | * | 9/2001 | Kashiwagi | 604/385.24 |
| 2003/0097110 A1 | * | 5/2003 | Erdman | 604/385.3 |
| 2005/0197643 A1 | * | 9/2005 | Suga et al. | 604/396 |

FOREIGN PATENT DOCUMENTS

CA 2 466 610 A1 * 6/2003
WO WO 02/34184 A1 * 5/2002

* cited by examiner

*Primary Examiner*—Tatyana Zalukaeva
*Assistant Examiner*—Susan Su
(74) *Attorney, Agent, or Firm*—Amster, Rothstein & Ebenstein LLP

(57) ABSTRACT

The present invention provides an absorbent garment subassembly for attaching to an absorbent garment, the absorbent garment having a front portion, a back portion and two side portions. The subassembly has a first carrier layer and an elastic member operatively associated with the first carrier layer. The elastic member has a center portion and two end portions. The center portion has a greater area than either of the end portions.

20 Claims, 7 Drawing Sheets

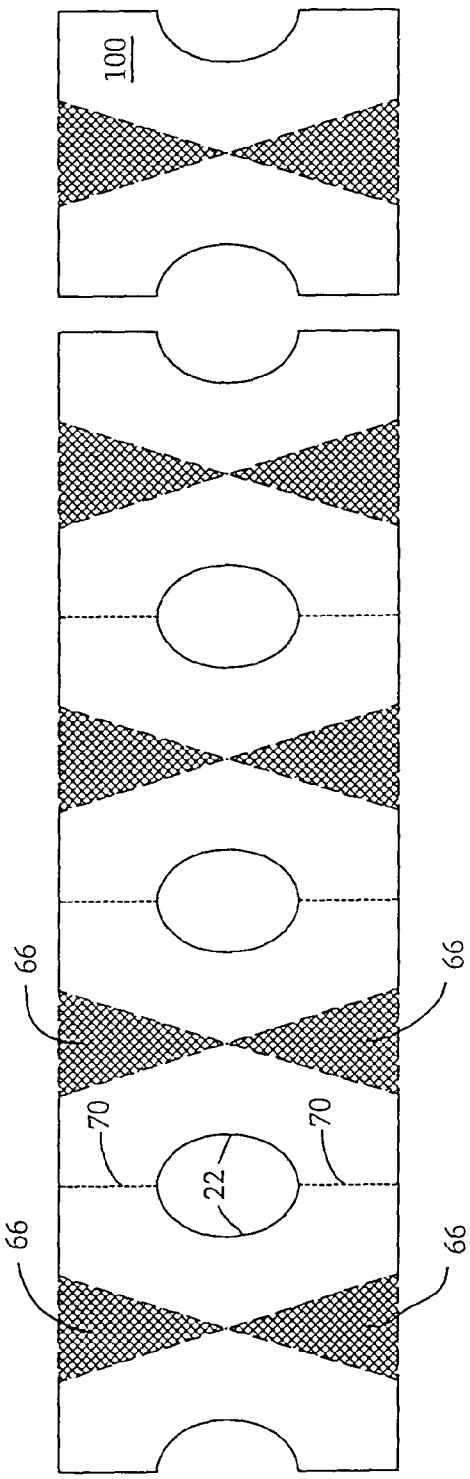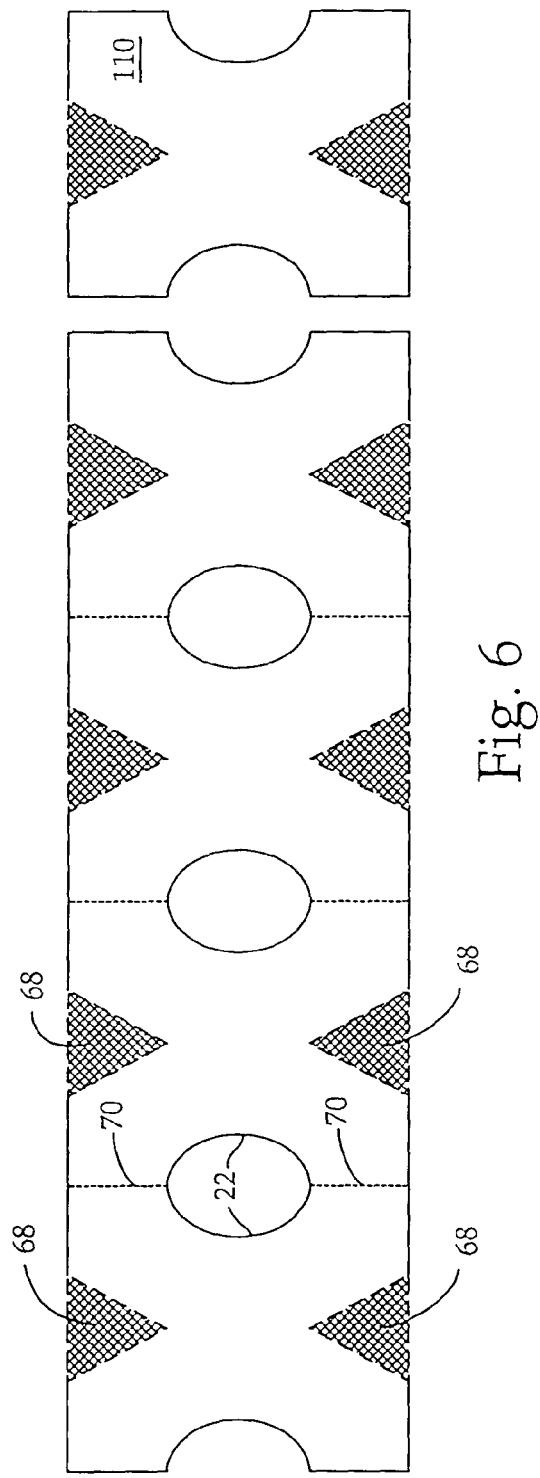

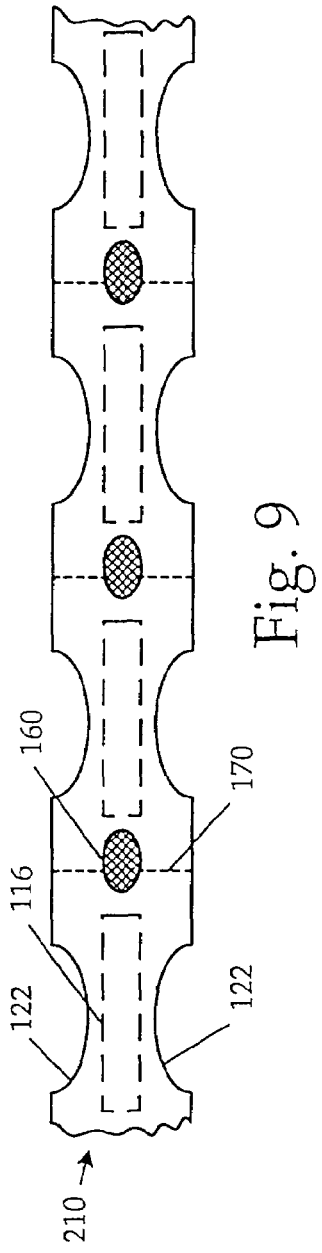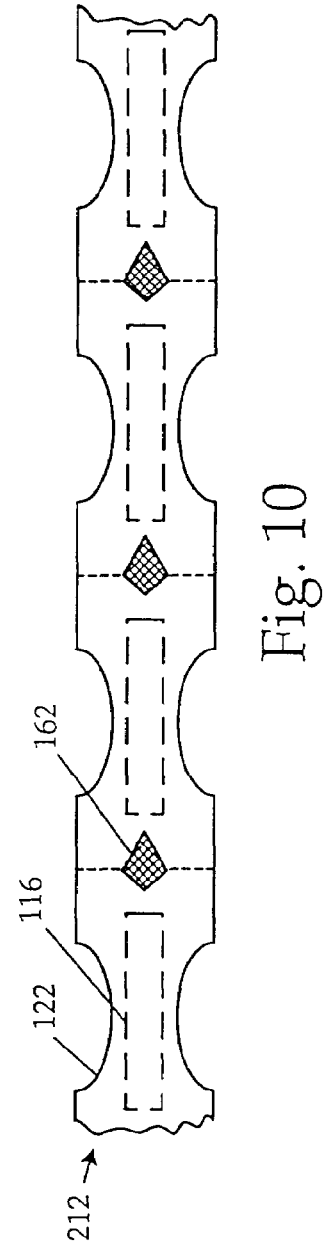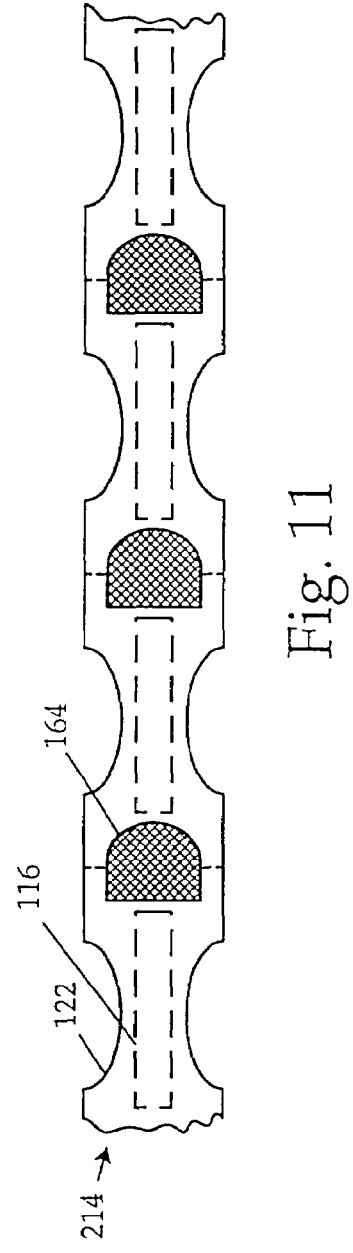

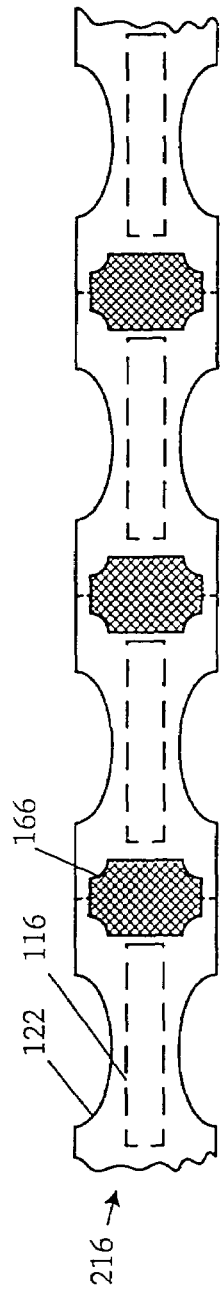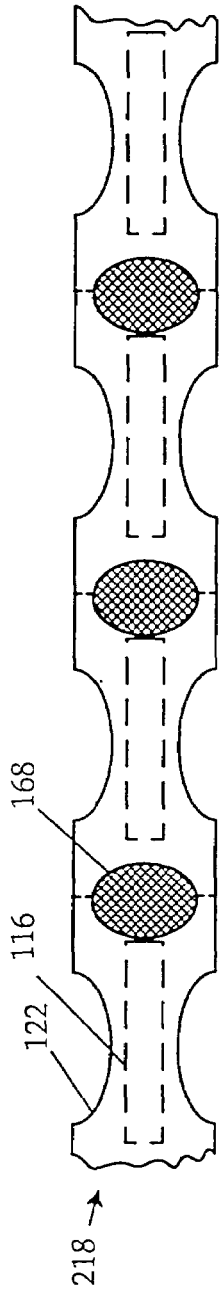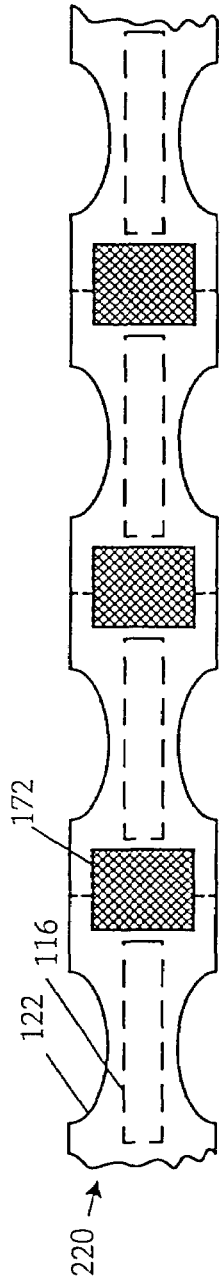

DISPOSABLE ARTICLE WITH CENTRALLY LOCATED ZONES OF ELASTICITY

This application is a divisional of U.S. patent application Ser. No. 09/989,447, filed Nov. 21, 2001 now abandoned, the disclosure of which is incorporated herein by reference thereto in its entirety.

FIELD OF THE INVENTION

The present invention generally relates to absorbent garments. In particular, it relates to absorbent garments having non-elastic side portions.

BACKGROUND OF THE INVENTION

Absorbent garments, such as diapers, adult incontinence products, training pants, and feminine care products, are in widespread use today.

The comfort level associated with wearing such garments is of great importance to the users of the garments. Most garments of this type include some sort of elastic material to help provide a snug, and therefore leak resistant, but still comfortable, fit.

SUMMARY OF THE INVENTION

The invention provides an absorbent article having a distribution of elastic material that, among other things, increases the comfort level experienced by the user of the garment and the esthetics of the fit of the garment.

Embodiments of the invention include an absorbent garment subassembly for attaching to an absorbent garment, the absorbent garment having a front portion, a back portion and two side portions. The subassembly has a first carrier layer and an elastic member operatively associated with the first carrier layer. The elastic member has a center portion and two end portions. The center portion has a greater area than either of the end portions.

Other embodiments of the invention include an absorbent article having a front portion, a back portion and two side portions. The article has a main chassis, an absorbent portion, and an elastic portion operatively associated with the main chassis. The elastic portion has a larger area in one of the front portion and the back portion than it does in either of the side portions.

Other embodiments of the invention include a method of making an absorbent article having a front portion, a back portion, two side portions, a main chassis, an absorbent portion, a first elastic portion operatively associated with the main chassis, and a second elastic portion operatively associated with the main chassis, the elastic portions having a larger area in one of the front portion and the back portion than in either of the side portions. The method moves the main chassis in a machine direction, applies the first elastic portion to the main chassis, and applies the second elastic portion to the main chassis. The elastic portions are shaped such that the elastic portions can be formed from a single ribbon of material with substantially no waste.

Other embodiments of the invention include a method of supplying first and second elastic portions for making an absorbent article having a front portion, a back portion, two side portions, a main chassis, an absorbent portion, the first elastic portion operatively associated with the main chassis, and the second elastic portion operatively associated with the main chassis, the elastic portions having a larger area in one of the front portion and the back portion than in either of the side portions. The method forms the elastic portions from a single ribbon of material with substantially no waste, re-indexes the elastic portions relative to each other, and transports the elastic portions to an assembly position of the article.

BRIEF DESCRIPTION OF THE DRAWINGS

FIG. 5 is a plan view of a plurality of garments in accordance with the invention;

FIG. 6 is a plan view of a plurality of garments in accordance with the invention;

FIG. 9 is a plan view of a plurality of garments in accordance with the invention;

FIG. 10 is a plan view of a plurality of garments in accordance with the invention;

FIG. 11 is a plan view of a plurality of garments in accordance with the invention;

FIG. 12 is a plan view of a plurality of garments in accordance with the invention;

FIG. 13 is a plan view of a plurality of garments in accordance with the invention; and FIG. 14 is a plan view of a plurality of garments in accordance with the invention.

DETAILED DESCRIPTION OF THE PREFERRED EMBODIMENTS

Figure 1:
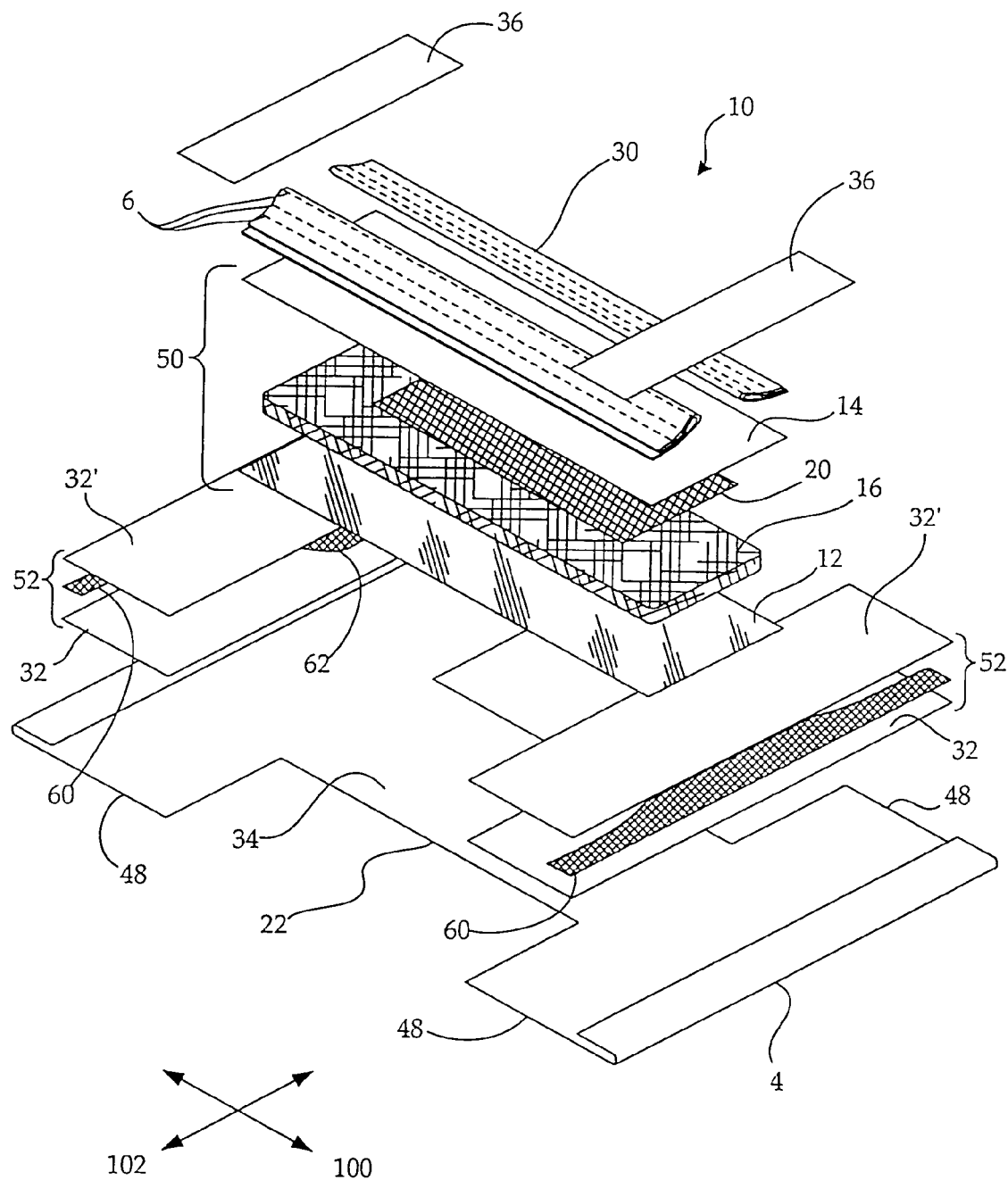
FIG. 1 is an exploded view of a garment in accordance with an embodiment of the invention.

"Garment," as used herein, refers to articles and garments that absorb and contain body exudates, and more specifically refers to articles and garments that are placed against or in proximity to the body of the wearer to absorb and contain the various exudates discharged from the user's body. A non-exhaustive list of examples of "absorbent articles" and garments includes diapers, diaper covers, disposable diapers, training pants, feminine hygiene products, and adult incontinence products. The invention can be used with all of the foregoing classes of absorbent articles and garments, without limitation, whether disposable or otherwise. Furthermore, the invention will be understood to encompass, without limitation, all classes and types of absorbent articles and garments, including those described above.

Throughout this description, the expressions "upper layer," "lower layer," "above" and "below," which refer to the various components included in the absorbent core units of the invention (including the layers surrounding the absorbent core units) are used merely to describe the spatial relationship between the respective components. The upper layer or component "above" the other component need not always remain vertically above the core or component, and the lower layer or component "below" the other component need not always remain vertically below the core or component. Indeed, embodiments of the invention include various configurations whereby the core is folded in such a manner that the upper layer ultimately becomes the vertically highest and vertically lowest layer at the same time. Other configurations are contemplated within the context of the present invention.

The term "component" can refer, but is not limited, to designated selected regions, such as edges, corners, sides or the like; structural members, such as elastic strips, absorbent pads, stretchable layers or panels, layers of material, or the like; or a graphic. The term "graphic" can refer, but is not limited, to any design, pattern, indicia or the like.

Throughout this description, the term "disposed" and the expressions "disposed on," "disposing on," "disposed in," "disposed between" and variations thereof (e.g., a description of the article being "disposed" is interposed between the words "disposed" and "on") are intended to mean that one element can be integral with another element, or that one element can be a separate structure bonded to or placed with or placed near another element. Thus, a component that is "disposed on" an element of the absorbent garment can be formed or applied directly or indirectly to a surface of the element, formed or applied between layers of a multiple layer element, formed or applied to a substrate that is placed with or near the element, formed or applied within a layer of the element or another substrate, or other variations or combinations thereof.

Throughout this description, the terms "topsheet" and "backsheet" denote the relationship of these materials or layers with respect to the absorbent core. It is understood that additional layers may be present between the absorbent core and the topsheet and backsheet, and that additional layers and other materials may be present on the side opposite the absorbent core from either the topsheet or the backsheet.

Throughout this description, center portions, front portions, back portions, side portions and end portions are described. It is noted that one skilled in the art will know based on the teachings of this disclosure where the boundaries between such portions are. In addition, the term "front portion" is used to describe a portion of the article that is generally near the belly region of the user, the term "back portion" is used to describe a portion of the article that is generally near the back region of the user, and the term "side portions" is used to describe the portions of the article that are generally near the sides of the user.

Absorbent garments and diapers may have a number of different constructions and configurations. In each of these, it generally is the case that an absorbent core is disposed between a liquid pervious, body-facing topsheet, and a liquid impervious, exterior facing backsheet. In some cases, one or both of the topsheet and backsheet may be shaped to form a pant-like garment. In other cases, the topsheet, backsheet and absorbent core may be formed as a discrete assembly that is placed on a main chassis and the chassis is shaped to form a pant-like garment. The garment may be provided to the consumer in the fully assembled pant-like shape, or may be partially pant-like and require the consumer to take the final steps necessary to form the final pant-like shape. In the case of training pant-type garments and most adult incontinent products, the garment is provided fully formed with factory-made side seams and the garment is donned by pulling it up the wearer's legs. In the case of diapers, a caregiver usually wraps the diaper around the wearer's waist and joins the side seams manually by attaching one or more adhesive or mechanical tabs, thereby forming a pant-like structure. The present invention is described herein with reference to both a training pant-type garment in which the topsheet, backsheet and absorbent core are assembled onto a chassis that forms a pant-like garment, and a diaper. Those skilled in the art will appreciate, however, that the invention may be used with other constructions.

Although the various embodiments of the invention are described in the context of a diaper, it is readily apparent and understood that this is not intended to limit the invention. The present invention may be used with any other absorbent garment having elastics incorporated therein.

Figure 2:
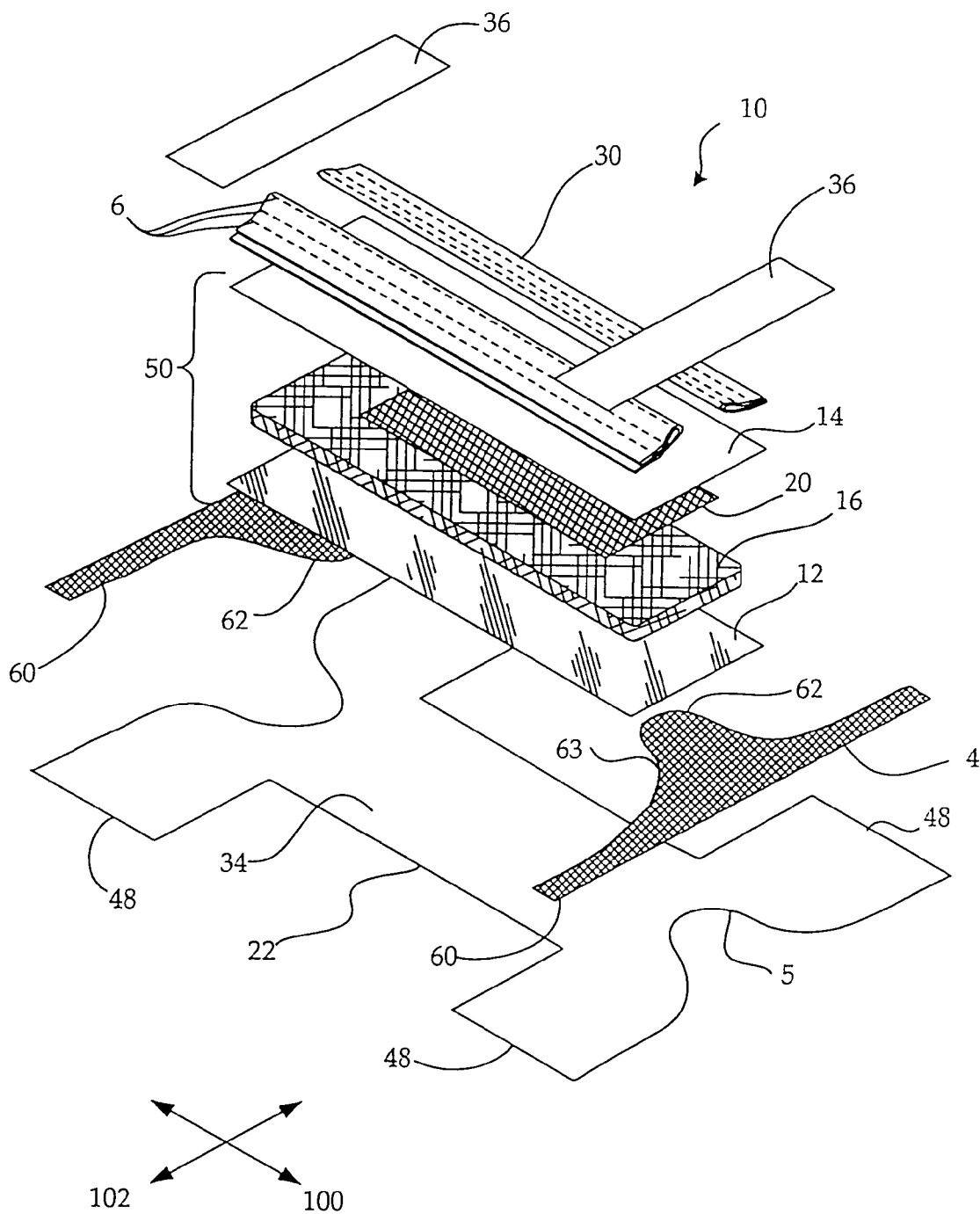
FIG. 2 is an exploded view of a garment in accordance with another embodiment of the invention.

The present invention is described generally with reference to FIGS. 1 and 2. FIGS. 1 and 2 are exploded views of embodiments of the present invention with elastic members shown in the elongated position for clarity, and the garment laid flat. The garment 10 has a longitudinal axis 100 corresponding approximately to the rear-to-front axis of the wearer, and a lateral axis 102, orthogonal to the longitudinal axis 100, and corresponding approximately to the side-to-side axis of the wearer.

In the embodiments of FIGS. 1 and 2, the garment 10 preferably comprises a main chassis 34 that forms a pant-like garment 10 having two leg hole cutouts 22 and longitudinal ends 4. The pant-like structure may be formed by joining lateral edge portions 48 to one another to form side seams. The lateral edge portions 48 may be joined during manufacture by any manner known in the art or combinations thereof. Examples of suitable joining mechanisms include: adhesives such as hot melt adhesives and construction adhesives, chemical or solvent bonding, stitching, heat bonding, autogenous bonding, and, preferably, ultrasonic welding. The lateral edge portions 48 also may be joined by a user with the assistance of adhesive strips or mechanical fasteners (not shown). When the lateral edge portions 48 are joined, leg hole cutouts 22 along the lateral edges of the garment 10 form leg holes, and the longitudinal ends 4 of the garment 10 form a waist encircling edge.

A core assembly 50 preferably is disposed on the interior of the chassis 34. The core assembly 50 may comprise an absorbent core 16 disposed between an exterior facing moisture impervious barrier film 12 or "backsheet," and a moisture pervious body-contacting inner layer 14 or "topsheet." Each of the backsheet 12, topsheet 14 and absorbent core 16 may comprise a plurality of layers of materials. In the embodiments depicted in FIGS. 1 and 2, the backsheet 12, topsheet 14, and absorbent core 16 comprise a subassembly that may be attached to the chassis 34. It should be readily apparent that in other embodiments one or both of the topsheet 14 and backsheet 12 may be shaped to form the main body of a pant-like garment thereby eliminating the need for a separate chassis 34. In still another embodiment of the invention, the backsheet 12, topsheet 14, and absorbent core 16 may be assembled and used without ever being shaped as a pant-like garment, such as when used as a feminine care product.

The chassis 34 may comprise a nonwoven polyethylene or polypropylene or any other suitable garment material known in the art or hereafter discovered. All or part of the chassis 34 may comprise a liquid pervious or liquid impervious material or a may be zone-treated to be partially liquid pervious or impervious. The chassis 34 may be stretched in one or more directions during the manufacturing process, thereby reducing its elasticity in the direction of stretch.

The backsheet 12 may comprise a laminate of multiple layers of materials that have similar or different properties. The backsheet 12 preferably is made from a substantially liquid impervious material. The selection and manufacture of such materials is well known in the art, and is disclosed, for example, in U.S. Pat. No. 6,123,694 issued to Peniak et al., and U.S. Pat. No. 6,176,952 issued to Maugans et al., each of which is incorporated herein by reference in its entirety, and in a manner consistent with the present invention. In one embodiment, the backsheet 12 is made from a thin thermoplastic material, such as a pigmented polyethylene film having a thickness in the range of 0.02-0.04 mm. The backsheet 12 may also have a laminate construction comprising one or more layers of meltblown polypropylene or meltblown polyethylene, sandwiched between layers of spun-bonded material (often referred to as an "SMS" laminate). Additional layers may be added to the backsheet 12 or the backsheet 12 may be treated with chemicals in order to provide it with other desirable properties, such as to improve the tactile feel, or "hand." The backsheet 12 may also be entirely or partly gas pervious to allow the garment to circulate air, or "breathe."

The topsheet 14, which preferably overlays the backsheet 12, can be made from a substantially liquid pervious material to allow body exudates to penetrate into the absorbent core 16. The topsheet 14 may typically comprise a carded polyester fiber with a latex binder or a spun-bonded polypropylene having continuous fibers and thermally bonded by patterned calendar rolls. The topsheet 14 may be treated over all or part of its surface to render it hydrophilic, and may also be zone-treated with a surfactant to render it hydrophilic only in certain target areas. The topsheet 14 also may be treated with skin treating ingredients, such as aloe, vitamin E, and the like, which can be accomplished by a variety of methods known in the art. The topsheet 14 also may comprise an apertured material, such as an apertured film.

In an embodiment of the present invention, one or more of the topsheet 14, backsheet 12 and chassis 34 may comprise a laminate of several layers of material, which may have different physical properties. In another embodiment, one or more of the topsheet 14, backsheet 12 and chassis 34 may comprise several pieces of material, which may have dissimilar physical properties, joined at or near their edges to form a multi-paneled sheet. Such an embodiment is disclosed, for example, in U.S. Pat. No. 5,275,590 issued to Huffman et al., which is incorporated herein by reference in its entirety, and in a manner consistent with the present invention.

In a preferred embodiment of the invention, the topsheet 14 and chassis 34 are comprised of a nonwoven material. The topsheet 14 may also be made, however, from any other suitable material. In various embodiments, one or more of the topsheet 14, backsheet 12 and chassis 34 may be selected to provide particular benefits to the garment 10. For example, they may be selected to provide a good tactile impression, or "hand," a comfortable fit, or gas permeability to improve the breathability of the garment 10.

The absorbent core 16 may be made from any absorbent material or materials known in the art. In one embodiment of the invention, the absorbent core 16 comprises wood fibers or other fibers such as chemical wood pulp, fibrous absorbent gelling material, or any other suitable liquid absorbing material, such as commercially available fluff pulp or fluffed bleached kraft softwood pulp or fibrous absorbent gelling material. In another embodiment of the invention, the absorbent core 16 comprises a combination of a porous fibrous web and super absorbent particles. Absorbent cores are known in the art and are disclosed, for example, in U.S. Pat. Nos. 5,281,207 and 6,068,620 issued to Chmielewski et al., U.S. Pat. No. 4,610,678 issued to Weisman et. al., U.S. Pat. No. 5,137,537 issued to Herron et. al., and U.S. Pat. No. 5,147,345 issued to Young et. al., which are incorporated herein by reference in their entirety, and in a manner consistent with the present invention. In such an embodiment, the absorbent core 16 may be surrounded by a liquid pervious tissue over-wrap (not shown), or other material.

The absorbent core 16 generally is elongated along the longitudinal axis 100 of the garment, and may extend along either or both of the lateral and longitudinal axes 102, 100 to the outer perimeter of the garment. In the embodiments depicted in FIGS. 1 and 2, the absorbent core 16 is substantially rectangular in shape, however, it may also have rounded ends or other shapes, such as an "I" shape or a "T" shape. The absorbent core 16 also may have channels, grooves or pockets, and may have a varying thickness.

The various parts of the garment 10 preferably are operatively associated with one another in such a manner that the garment will maintain its desired structure during use. The parts may be operatively associated with one another by a variety of methods known in the art, including, but not limited to: using adhesives such as hot melt adhesives and construction adhesives, chemical or solvent bonding, ultrasonic welding, stitching, heat bonding, autogenous bonding, or any other method of affixation known or hereafter discovered. U.S. Pat. No. 4,919,738 issued to Ball et. al. discloses a method of autogenous bonding, and its disclosure is herein incorporated by reference in its entirety in a manner consistent with the invention. All of the parts may be joined to each adjacent part, but some parts may not be joined to others. In one embodiment, the topsheet 14 and backsheet 12 are bonded to one another around their perimeter regions, thereby encasing and holding the absorbent core 16 in place without having to directly join the absorbent core 16 to any other component parts of the garment 10. The topsheet 14 or backsheet 12 may also be operatively associated with the absorbent core 16. As understood herein, the term "operatively associated" includes directly joining one part to another, indirectly joining parts together through one or more intermediary parts, whether those intermediary parts are described herein or not, joining parts in such a manner that unjoined parts are captured or held in their proper place, and any other suitable joining means that maintains the structural integrity of the garment 10 for the duration of its use.

In the embodiments of the invention depicted in FIGS. 1 and 2, the garment 10 further comprises various mechanisms for improving the garment's ability to contain body exudates, such as standing leg gathers 30. Standing leg gathers 30 may be formed by incorporating a plurality of gather elastics 6 into folds in the topsheet 14 or into additional ribbons (not shown) that are attached to the garment near the leg hole cutouts 22. The gather elastics 6 cause the standing leg gathers 30 to rise above the interior surface of the garment 10, thereby forming vertical curtains of material that help contain exudates. The ribbons may be liquid pervious or liquid impervious, and more than one set of standing leg gathers 30 may be provided. The standing leg gathers 30 may be attached to the topsheet 14, backsheet 12, chassis 34 or any other suitable part of the garment such that they block or impede the passage of fluids and other exudates. Additional elastics (not shown) may also be incorporated into the chassis 34, topsheet 14 or backsheet 12 adjacent the leg holes to form conventional (i.e., non-standing) leg gathers, as is known in the art. Conventional gathers contract the garment 10 around the wearer's legs and body to prevent leakage. U.S. Pat. Nos. 3,860,003 and 4,081,301 issued to Buell, U.S. Pat. No. 4,695,278 issued to Lawson, U.S. Pat. No. 4,808,177 issued to Des Marais, U.S. Pat. No. 4,795,454 issued to Dragoo, and U.S. Pat. No. 4,938,755 issued to Foreman illustrate other embodiments of leg cuffs and gathers in absorbent garments, and the disclosures of each of these patents are hereby incorporated by reference in their entirety.

The core assembly 50 may comprise additional layers of material that may reduce rewet of the topsheet 14, reduce strikethrough times or otherwise improve the absorbency, dryness and other properties of the garment 10. For example, a transfer layer 20 comprising an apertured film or an air-bonded carded, bicomponent fiber nonwoven, having a basis weight of about 40 g/m² may be disposed between the topsheet 14 and the absorbent core 16. Such multiple layer absorbent cores are known in the art and disclosed in U.S. Pat. No. 5,439,458 issued to Noel et al., which is incorporated herein by reference in its entirety, and in a manner consistent with the present invention.

The core assembly 50 may be attached to the chassis 34 by any manner known in the art, such as by ultrasonic bonding or by the use of lines of hot melt adhesive. The bond between the core assembly 50 and the chassis 34 may be reinforced by laterally-extending end strips 36 that are applied over the longitudinal ends of the core assembly 50 and bonded to the underlying structure of the garment 10. The end strips 36 may also hold the ends of the standing leg gathers 30. Such end strips 36 preferably comprise a fluid pervious nonwoven material, but may be fluid impervious or a material other than a nonwoven material. Such materials are known in the art. The end strips 36 may also help prevent the longitudinal flow of exudates past the ends of the core assembly 50, particularly if the edges of the nonwoven strips overlying the core assembly 50 are left unbonded so that they form pockets to hold exudates.

In other embodiments, adjustment strips (not shown) may be disposed on and partially attached to the garment to provide for an adjustable fit. Absorbent garments often loosen during use for various reasons, such as inelastic stretching of the various components, changes in user size, and increased loading caused by the release of body exudates into the garment 10. The adjustment strips may be formed such that they may be releasably attached to the garment 10 to reduce the circumference of the waist encircling edge, and may comprise any fastening mechanism known in the art or later discovered.

It often is desirable for an absorbent garment to contract around various parts of the wearer's body to provide improved comfort and exudate containment. In addition to the standing leg gathers 30 or conventional gathers, waist elastics and tummy elastics may be incorporated into the garment 10 to contract the garment 10 about the wearer's waist and stomach. Such elastics are typically stretched as they are joined to the garment 10 so that the contraction of the elastics causes the garment 10 to contract about the wearer. The elastics may also be applied in an unstretched stated then mechanically stretched to create an elasticized region in the garment (often called a zero-strain laminate). The elastics also may be applied in an inelastic state then heat activated to cause them to be come elasticized. The elastics may be made from natural or synthetic rubber, elastomers, LYCRA® elastomer (available from E.I. DuPunt de Nemours and Company, a business having offices in Wilmington, Del.), polyurethane, heat shrinkable polymer ribbons, or any other suitable elastic material or composite.

Examples of elastics in accordance with particularly preferred embodiments of the invention are shown in FIGS. 1 and 2. In FIG. 1, elastic units 52 are attached to the chassis 34 near longitudinal ends 4. In this example, each elastic unit 52 has an elastic portion 60 disposed between a first carrier layer 32 and a second carrier layer 32'. Each elastic portion 60 has a central portion 62, which is shown more clearly in FIG. 2 and, therefore, discussed below with reference to that figure. In FIG. 1, first and second carrier layers 32, 32' can serve several purposes. First, the carrier layers help maintain elastic portion 60 in its proper shape and orientation during assembly of the garment. Also, second carrier layer 32' can provide a barrier between the user and elastic portion 60 that is more comfortable to the user's skin than elastic portion 60. While two carrier layers are shown in FIG. 1, it is noted that elastic portion 60 can be provided with no carrier layer (as shown in FIG. 2) or with only first carrier layer 32 or second carrier layer 32'. Examples of suitable elastic portion 60 and elastic unit 52 are an elastic scrim between two layers of non-woven material and an elastic film ultrasonically bonded to, and between, two layers of non-woven material.

As shown more clearly in FIG. 2, elastic portions 60 have a central portion 62 that protrudes in a direction toward a central or crotch, portion of the garment. By providing more elastic material in central portion 62 than in other areas of elastic portions 60, a stronger elastic force is present at the belly and back areas as opposed to the side areas of a user wearing the garment. This distribution of elastic forces can produce a more comfortable and secure garment. In addition, placing elastic in the center portion of the absorbent garment instead of the sides makes the sides more comfortable on the skin of the user and provides better fit and less slippage of the garment after it contains exudates. Although two similar elastic portions 60 are shown in FIGS. 1 and 9, it is noted that only one elastic portion may be provided or, if two elastic portions are provided, they may be different shapes and/or sizes.

Also, it is noted that elastic portion 60 (with or without carrier layers 32 and/or 32') can be applied to chassis 34 (as shown in FIG. 1) or can take the place of a portion of chassis 34 (as shown in FIG. 2). In FIG. 2, an edge 63 of elastic portion 60 attaches to an edge 5 of chassis 34. This attachment can be an edge-to-edge attachment or an overlap attachment.

Figure 3:
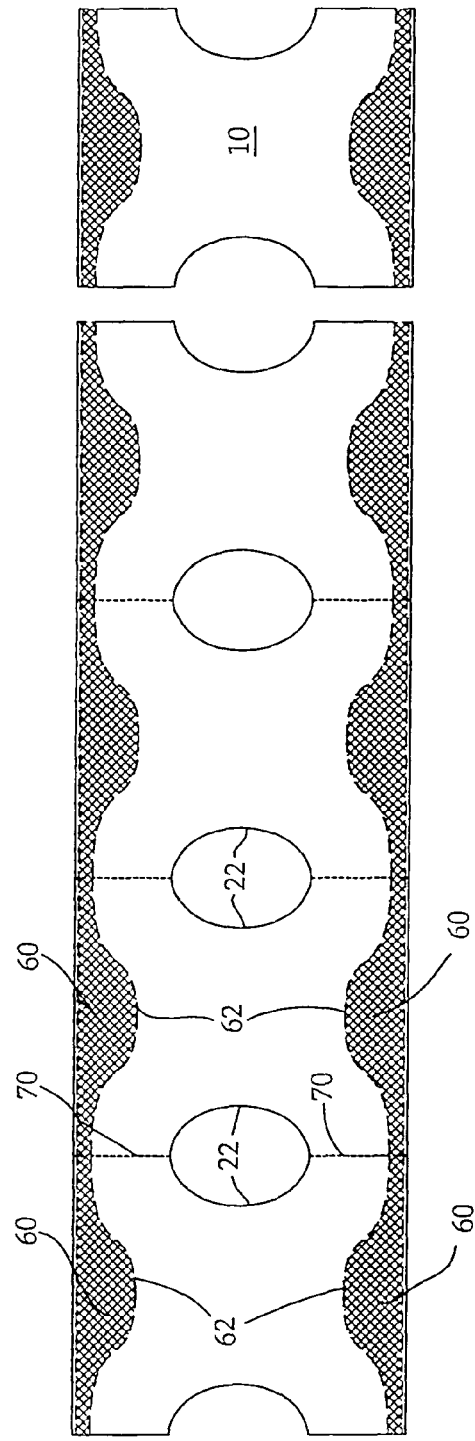
FIG. 3 is a plan view of a plurality of garments in accordance with the invention.
Figure 4:
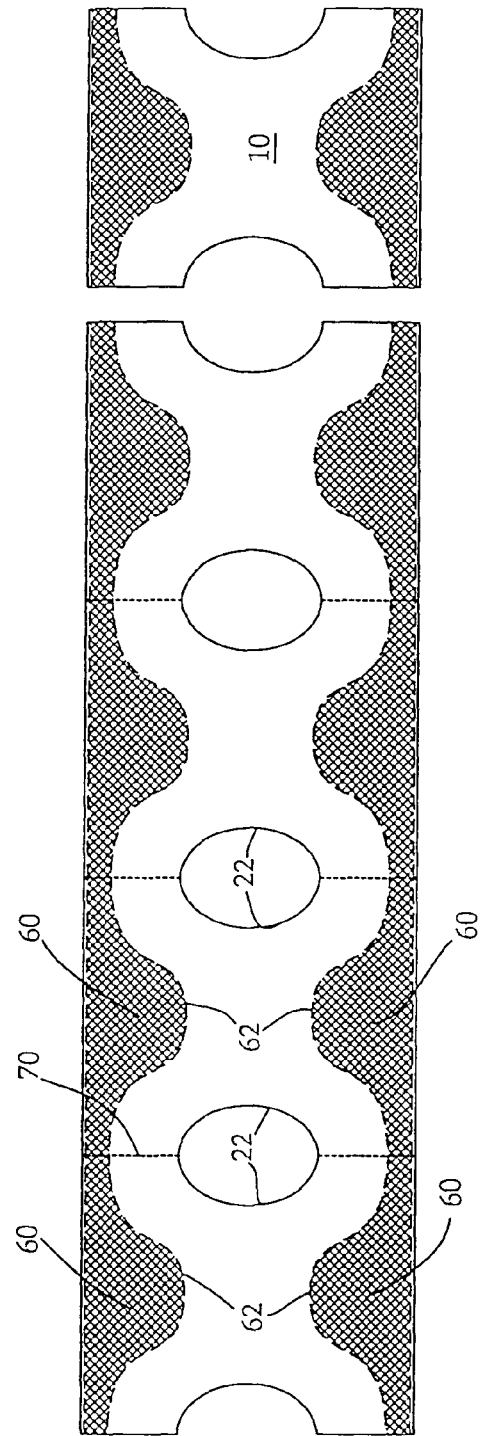
FIG. 4 is a plan view of a plurality of garments in accordance with the invention.

FIGS. 3-6 each show a plurality of garments as they would be positioned during manufacturing. FIGS. 3 and 4 show garments 10 that, during manufacturing, are separated from one another along seams 70. In FIG. 3, garments 10 each have two elastic portions 60 with central portions 62 of a given size. FIG. 4 shows garments 10 similar to the garments shown in FIG. 3, however, central portions 62 of elastic portions 60 protrude farther toward a central, or crotch, portion of the garments.

FIG. 5 shows garments 100 each having two elastic portions 66. In this example, triangular shaped elastic portions 66 contact each other at a central, or crotch, portion of garment 100. FIG. 6 shows garments 110 having triangular elastic portions 68 that do not contact each other. Considerations such as amount of elastic force desired, preferred location of elastic force, cost of elastic material and production efficiency go into determining the size of the elastic portions and whether they touch each other. Those skilled in the art are capable of configuring the elastics in any suitable manner in accordance with the invention, using the guidelines provided herein.

Figure 7:
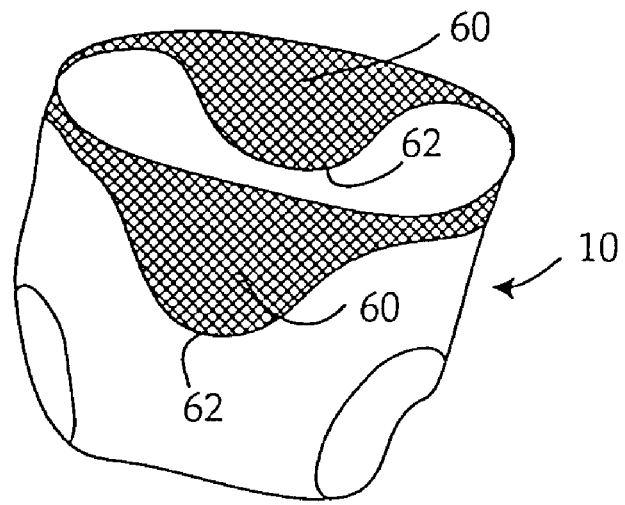
FIG. 7 is a perspective view of a garment in accordance with the invention.
Figure 8:
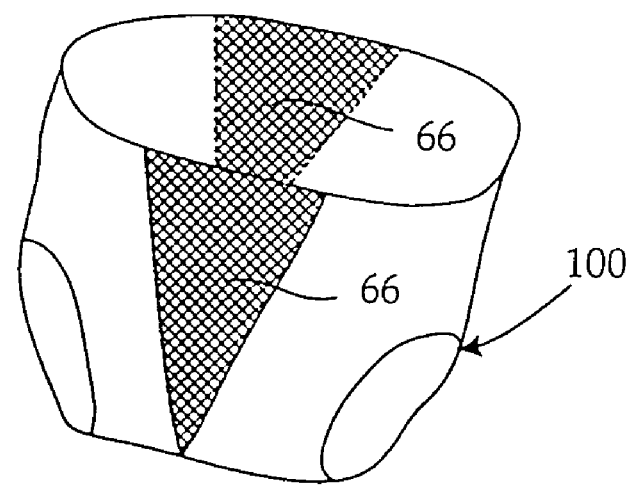
FIG. 8 is a perspective view of a garment in accordance with the invention.

FIGS. 7 and 8 show assembled examples of the garments shown in FIGS. 4 and 5, respectively, with only the elastics shown for purposes of clarity. These garments can be preassembled, as in a pant, or secured in place by the user, as in a diaper.

FIGS. 9-14 show examples of garments manufactured with a machine direction parallel to a longitudinal axis of the garment and corresponding approximately to the rear-to-front axis of the wearer. In these figures, the machine direction extends horizontally from the left to the right. FIG. 9 shows garments 210, each having an absorbent core 116 and leg hole cutouts 122. An elastic portion 160 is positioned between two adjacent garments 210 over seam 170. Upon cutting the garments 210 apart from one another, elastic portion 160 will be cut to form two elastic portions, one at the front of a garment and the other at the rear of the adjacent garment. In this example, elastic portion 160 is positioned asymmetrically relative to seam 170. However, elastic portion 160 could be positioned symmetrically relative to seam 170.

FIG. 10 shows garments 212 similar to garments 210 shown in FIG. 9 except that elastic portions 162 have a diamond shape. Elastic portions 162 are shown as being asymmetrical relative to seam 170 but could be made symmetrical to seam 170. FIG. 11 shows garments 214 similar to garments 210 shown in FIG. 9 except that elastic portion 164 is "D" shaped. As with FIGS. 9 and 10, the elastic portions shown in FIG. 11 can be shifted relative to seam 170 to provide the desired elastic force in the front and back of the garment.

FIGS. 12-14 show further examples of elastic portions 166, 168, 172 on garments 216, 218, 220, respectively. As with the elastic portions in FIGS. 9-11, elastic portions 166, 168, 172 can be positioned at various locations relative to seam 170 to provide the desired distribution of elastic force. In addition, the sizes of the elastic portions shown in FIGS. 9-14 can be altered to provide the desired elastic force.

As mentioned above, efficiency of manufacturing can be improved by properly designing the size and shape of the elastic portions. For example, the elastic portions shown in FIGS. 3-6 and 14 can be cut from a ribbon of elastic material with no waste. In the cases of the elastic portions shown in FIGS. 3-6, the elastic portions placed on one side (for example, the upper side in the figures) may need to be offset relative to the position of the elastic portions on the other side of the garment (for example, the bottom side in the figures) in order for there to be substantially no waste in their production. Substantially no waste in the context of the invention denotes less than 5% by weight loss of material to waste, and preferably less than 1% by weight loss of material. For example, elastic portions similar to those shown in FIGS. 3 and 4 can be produced with substantially no waste by cutting a ribbon having parallel edges along a sine wave, separating the two portions and shifting one portion one half phase relative to the other portion. The triangular elastic portions shown in FIGS. 5 and 6 can be similarly produced although a plurality of individual pieces result instead of two continuous ribbons.

While the invention has been described with reference to particular embodiments and examples, those skilled in the art will appreciate that various modifications may be made thereto without significantly departing from the spirit and scope of the invention.

What is claimed is:

1. An absorbent article having a front portion, a back portion, a crotch portion, and two side portions, the article comprising:
   a main chassis;
   an absorbent portion; and
   first and second substantially elastic portions which replace a portion of the main chassis, each of said first and second substantially elastic portions having a first region that overlaps a portion of the main chassis for attachment thereto and a second region that does not overlap the main chassis, wherein the first substantially elastic portion has a first central elastic portion corresponding to the front portion of the article and two first side inelastic portions corresponding to the side portions of the article, and the second substantially elastic portion has a second central elastic portion corresponding to the back portion of the article and two second side inelastic portions corresponding to the side portions of the article, and wherein said first central elastic portion contacts said second central elastic portion and extends in a longitudinal direction towards the crotch portion of the article.

2. The article of claim 1, wherein the first region has an area that is smaller than an area of the second region.

3. The article of claim 2, wherein the area of the first region is less than ten percent of a total area of the elastic portion.

4. The article of claim 1, wherein the first central elastic portion has a depth measured from a waist edge of the article toward a crotch portion of the article, the first side inelastic portions have a depth measured from the waist edge of the article toward the crotch portion of the article, and the depth of the first central elastic portion is greater than the depth of the first side inelastic portions.

5. The article of claim 4, wherein the second central elastic portion has a depth measured from the waist edge of the article toward the crotch portion of the article, the second side inelastic portions have a depth measured from the waist edge of the article toward the crotch portion of the article, and the depth of the second central elastic portion is greater than the depth of the second side inelastic portions.

6. The article of claim 1, wherein the second central elastic portion has a depth measured from a waist edge of the article toward a crotch portion of the article, the second side inelastic portions have a depth measured from the waist edge of the article toward the crotch portion of the article, and the depth of the second central elastic portion is greater than the depth of the second side inelastic portions.

7. The article of claim 1, wherein the first central elastic portion contacts the second central elastic portion at the crotch portion of the article.

8. The article of claim 7, wherein the first and second elastic portions are triangular in shape.

9. The article of claim 1, wherein the first and second elastic portions are triangular in shape.

10. The article of claim 1, wherein the first and second elastic portions have different areas.

11. The article of claim 1, wherein the first and second elastic portions are one of oval and circular in shape.

12. The article of claim 1, wherein the first and second elastic portions are diamond shaped.

13. The article of claim 1, wherein the first and second elastic portions are rectangular.

14. The article of claim 1, wherein the article is a diaper.

15. The article of claim 1, wherein the article is a pant.

16. The absorbent article of claim 1, wherein the article further comprises a first carrier layer operatively associated with at least one of the first and second elastic portions.

17. The absorbent article of claim 1, wherein a longitudinal dimensions of at least one of the first and second elastic portions along the longitudinal direction is a first distance, a longitudinal dimension of each of the associated side portions for the first and second elastic portions along the longitudinal direction is a second distance, and the first distance is less than twice the second distance.

18. The absorbent article of claim 1, wherein a lateral dimension of at least one of the first and second elastic portions perpendicular to the longitudinal direction is a third distance, a lateral dimension of each of the two associated side portions of the first and second elastic portions perpendicular to the longitudinal direction is a fourth distance, and the third distance is greater than the fourth distance.

19. The absorbent article of claim 1, wherein a lateral dimension of at least one of the first and second elastic portions perpendicular to the longitudinal direction is a first distance, a lateral dimension of each of the associated side portions of the first and second elastic portions perpendicular to the longitudinal direction is a second distance, and the first distance is greater than twice the second distance.

20. The absorbent article of claim 1, further comprising a second carrier layer operatively associated with the elastic portion wherein the elastic portion is disposed between the first and second carrier layers.

* * * * *